United States Patent
MacDonald et al.

(10) Patent No.: US 7,262,188 B2
(45) Date of Patent: Aug. 28, 2007

(54) PHENYL SULFONE DERIVATIVES AND THEIR USE IN THE TREATMENT OF CNS DISORDERS

(75) Inventors: Gregor James MacDonald, Harlow (GB); Mervyn Thompson, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 58 days.

(21) Appl. No.: 10/547,987

(22) PCT Filed: Mar. 9, 2004

(86) PCT No.: PCT/EP2004/002554

§ 371 (c)(1),
(2), (4) Date: Sep. 8, 2005

(87) PCT Pub. No.: WO2004/080986

PCT Pub. Date: Sep. 23, 2004

(65) Prior Publication Data
US 2006/0281757 A1 Dec. 14, 2006

(30) Foreign Application Priority Data
Mar. 11, 2003 (GB) ................. 0305575.3

(51) Int. Cl.
*A61K 31/55* (2006.01)
*A61K 31/495* (2006.01)
*C07D 243/08* (2006.01)
*C07D 295/112* (2006.01)

(52) U.S. Cl. ............... 514/218; 514/255.03; 540/575; 544/395

(58) Field of Classification Search ............ None
See application file for complete search history.

(56) References Cited

U.S. PATENT DOCUMENTS

| 5,627,077 A | 5/1997 | Dyllick-Brenzinger et al. .............. 436/106 |
| 5,665,739 A | 9/1997 | Lang et al. ................ 514/345 |
| 5,726,177 A | 3/1998 | Halazy et al. ............. 514/253 |

FOREIGN PATENT DOCUMENTS

| EP | 0930302 B1 | 4/2003 |
| WO | WO99/02505 | 1/1999 |
| WO | WO99/37623 | 7/1999 |
| WO | WO03/014097 | 2/2003 |

OTHER PUBLICATIONS

Robichaud et al. in Annual Reports in Medicinal Chemistry, vol. 36, p. 11-20 (2000).*
Rogers et al. Psychopharmacology, vol. 158, p. 114-119 (2001).*
Vippagunta et al. Advanced Drug Delivery Reviews, vol. 48, pp. 3-26 (2001).*
Bromidge et al. "Phenyl benzenesulfonamides are novel and selective 5-HT6 antagonists: identification of N-(2,5-dibromo-3-fluorophenyl)-4-methoxy-3-piperazi n-1-ylbenzenesulfonamide" Bioorganic & Medicinal Chemistry Letter vol. 11, No. 1 2001 pp. 55-58.
Bentley et al. *British Journal of Pharmacology Supplement*, 126: 66 (1999).
Bentley et al. *Journal of Psychopharmacology Supplement*, A64: 255 (1997).

* cited by examiner

*Primary Examiner*—Emily Bernhardt
(74) *Attorney, Agent, or Firm*—Kathryn L. Sieburth; Mary E. McCarthy; Charles M. Kinzig

(57) ABSTRACT

This invention relates to novel phenyl sulfone compounds having pharmacological activity, processes for their preparation, to compositions containing them and to their use in the treatment of CNS and other disorders.

4 Claims, No Drawings

PHENYL SULFONE DERIVATIVES AND THEIR USE IN THE TREATMENT OF CNS DISORDERS

This invention relates to novel phenyl sulfone compounds having pharmacological activity, processes for their preparation, to compositions containing them and to their use in the treatment of CNS and other disorders.

WO 99/37623 (SmithKline Beecham pic) and EP 930302 (F. Hoffman La Roche) both describe a series of piperazinyl benzenesulfone derivatives which are claimed to have affinity for the 5-HT$_6$ receptor. DE 4238994 (BASF) describes a series of benzenesulfone derivatives which are claimed to be useful as markers for fingerprinting petroleum and petroleum products. EP602523 (Hoechst) describes a series of benzoyl guanidine derivatives which are claimed to be useful in a variety of cardiovascular disorders. WO 95/14004 (Pierre Fabre Medicament) describes a series of indolyl derivatives which are claimed to have affinity for the 5-HT$_1$ receptor.

A structurally novel class of compounds has now been found which also possess affinity for the 5-HT$_6$ receptor. The present invention therefore provides, in a first aspect, a compound of formula (I) or a pharmaceutically acceptable salt thereof:

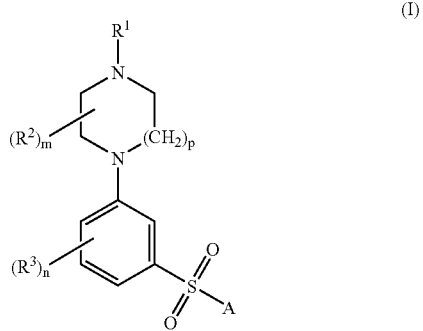

(I)

wherein:
$R^1$ and $R^2$ independently represent hydrogen or $C_{1-6}$ alkyl or $R^1$ is linked to $R^2$ to form a group $(CH_2)_2$, $(CH_2)_3$ or $(CH_2)_4$;
$R^3$ independently represents hydrogen, halogen, $C_{1-6}$alkyl, $C_{3-6}$cycloalkyl, $C_{1-6}$alkoxy, $C_{1-6}$ alkylthio, $C_{1-6}$ alkylsulfinyl, $C_{1-6}$alkylsulfonyl, $C_{1-6}$alkanoyl, CN, CF$_3$, OCH$_2$CF$_3$, OCF$_3$, hydroxyC$_{1-6}$alkyl, hydroxyC$_{1-6}$alkoxy, $C_{1-6}$alkoxycarbonyl, $C_{1-6}$alkoxyC$_{1-6}$alkoxy, nitro, amino, $C_{1-6}$alkylamino, diC$_{1-6}$alkylamino or NR$^4$COR$^5$, where $R^4$ and $R^5$ are independently hydrogen or $C_{1-6}$ alkyl;
m represents an integer from 1 to 5, such that wherein m is an integer greater than 1, said $R^2$ groups may optionally be linked to form a group CH$_2$, (CH$_2$)$_2$ or (CH$_2$)$_3$;
n represents an integer from 1 to 4;
p represents 1 or 2;
A represents a group —Ar$^1$ or —Ar$^2$Ar$^3$;
Ar$^1$ represents unsubstituted phenyl, naphthyl optionally substituted by 1, 2 or 3 substituents or monocyclic heteroaryl linked to the SO$_2$ group via a carbon atom and optionally substituted by 1, 2 or 3 substituents;
Ar$^2$ represents phenyl or a monocyclic heteroaryl group linked to the SO$_2$ group via a carbon atom, each of which may be optionally substituted by 1, 2 or 3 substituents;
Ar$^3$ represents a monocyclic heteroaryl group optionally substituted by 1, 2 or 3 substituents;
substituents on Ar$^1$, Ar$^2$ and Ar$^3$ are independently selected from the group consisting of halogen, hydroxy, cyano, nitro, trifluoromethyl, trifluoromethoxy, $C_{1-6}$alkyl, trifluoromethanesulfonyloxy, pentafluoroethyl, $C_{1-6}$alkoxy, arylC$_{1-6}$alkoxy, $C_{1-6}$alkylthio, $C_{1-6}$alkoxyC$_{1-6}$alkyl, $C_{3-7}$cycloalkylC$_{1-6}$alkoxy, $C_{1-6}$alkanoyl, $C_{1-6}$alkoxycarbonyl, $C_{1-6}$alkylsulfonyl, $C_{1-6}$alkylsulfinyl, $C_{1-6}$alkylsulfonyloxy, $C_{1-6}$alkylsulfonylC$_{1-6}$alkyl, arylsulfonyl, arylsulfonyloxy, arylsulfonylC$_{1-6}$alkyl, $C_{1-6}$alkylsulfonamido, $C_{1-6}$alkylNHCO—, $C_{1-6}$alkylCONH—C$_{1-6}$ alkylsulfonamidoC$_{1-6}$alkyl, $C_{1-6}$alkylNHCOC$_{1-6}$alkyl-, $C_{1-4}$alkylCONHC$_{1-6}$alkyl-, arylsulfonamido, arylCONH—, arylNHCO—, arylsulfonamidoC$_{1-6}$ alkyl, arylCONHC$_{1-6}$alkyl, arylNHCOC$_{1-6}$alkyl, aroyl, aroylC$_{1-6}$alkyl, arylC$_{1-6}$ alkanoyl, or a group CONR$^6$R$^7$ or SO$_2$NR$^6$R$^7$, wherein R$^6$ and R$^7$ independently represent hydrogen or $C_{1-6}$alkyl or together may be fused to form a 5- to 7-membered aromatic or non-aromatic heterocyclic ring optionally interrupted by an O or S atom; or solvates thereof.

In one particular aspect of the present invention, there is provided a compound of formula (I) as defined above wherein p represents 1.

Specific compounds of formula (I) which may be mentioned are those wherein A represents Ar$^1$, Ar$^1$ represents unsubstituted phenyl and R$^3$ represents halogen or CF$_3$.

Alkyl groups, whether alone or as part of another group, may be straight chain or branched and the groups alkoxy and alkanoyl shall be interpreted similarly. Alkyl moieties are more preferably $C_{1-4}$alkyl, eg. methyl or ethyl. The term 'halogen' is used herein to describe, unless otherwise stated, a group selected from fluorine, chlorine, bromine or iodine.

The term "aryl" includes phenyl and naphthyl.

The term "monocyclic heteroaryl" is intended to mean a 5-7 membered monocyclic aromatic ring containing 1 to 3 heteroatoms selected from oxygen, nitrogen and sulfur. Suitable examples of such monocyclic aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Heteroaryl groups, as described above, may be linked to the remainder of the molecule via a carbon atom or, when present, a suitable nitrogen atom except where otherwise indicated above.

It will be appreciated that wherein the above mentioned aryl or heteroaryl groups have more than one substituent, said substituents may be linked to form a ring, for example a carboxyl and amine group may be linked to form an amide group.

Preferably R$^1$ represents hydrogen or methyl, most preferably hydrogen.

Preferably R$^2$ represents hydrogen or methyl, most preferably hydrogen.

Preferably R$^3$ represents hydrogen or halogen, most preferably hydrogen or a chlorine atom.

Preferably m and n both represent 1.
Preferably p represents 1.
Preferably A represents a group —Ar$^1$.
When A represents a group —Ar$^1$, Ar$^1$ preferably represents unsubstituted phenyl.

Preferred compounds according to the invention include examples E1-E3 as shown below, or a pharmaceutically acceptable salt thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. The present invention includes within its scope all possible stoichiometric and non-stoichiometric forms.

The compounds of formula (I) may be prepared in crystalline or non-crystalline form, and, if crystalline, may optionally be solvated, eg. as the hydrate. This invention includes within its scope stoichiometric solvates (eg. hydrates) as well as compounds containing variable amounts of solvent (eg. water).

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises:
(a) reacting a compound of formula (II)

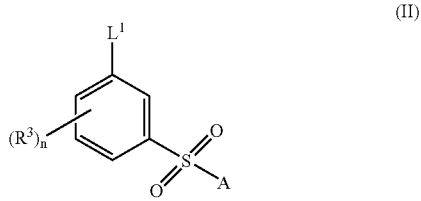

wherein $R^3$, n and A are as defined above and $L^1$ represents a suitable leaving group such as a halogen atom (e.g. a chlorine, bromine or iodine atom) or a trifluoromethylsulfonyloxy group, with a compound of formula (III)

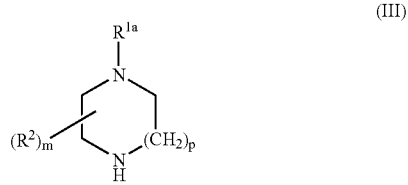

wherein $R^2$, m and p are as defined above and $R^{1a}$ is as defined for $R^1$ or represents a suitable N-protecting group (such as t-butyloxycarbonyl (Boc), methyl or benzyloxycarbonyl) and thereafter as necessary removing an $R^{1a}$ N-protecting group; or
(b) deprotecting a compound of formula (I) which is protected; and optionally thereafter
(c) interconversion to other compounds of formula (I).

Process (a) typically comprises the use of a palladium, nickel or copper catalyst, for example a mixture of a palladium source such as $Pd_2(dba)_3$ and a suitable ligand such as 2 2,2'-bis(diphenylphosphino)-1,1'-binaphthyl (BINAP) or (2-dicyclohexylphosphanylphenyl)-dimethylamine, together with a suitable base such as sodium t-butoxide or cesium carbonate, in an inert solvent such as 1,4-dioxane.

In process (b), examples of protecting groups and the means for their removal can be found in T. W. Greene 'Protective Groups in Organic Synthesis' (J. Wiley and Sons, 1991). Suitable amine protecting groups include sulfonyl (e.g. tosyl), acyl (e.g. acetyl, 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl (—$COCF_3$) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid. A further amine protecting group includes methyl which may be removed using standard methods for N-dealkylation (e.g. 1-chloroethyl chloroformate under basic conditions followed by treatment with methanol).

Process (c) may be performed using conventional interconversion procedures such as epimerisation, oxidation, reduction, alkylation, nucleophilic or electrophilic aromatic substitution, ester hydrolysis or amide bond formation. For example, N-dealkylation of a compound of formula (I) wherein $R^1$ represents an alkyl group to give a compound of formula (I) wherein $R^1$ represents hydrogen. It will be appreciated that such interconversion may be interconversion of protected derivatives of formula (I) which may subsequently be deprotected following interconversion.

Compounds of formula (II) may be prepared by reaction of a compound of formula (IV)

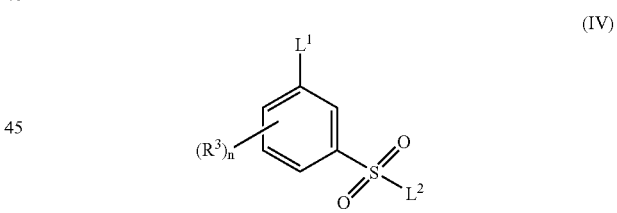

wherein $R^3$, n and $L^1$ are as defined above and $L^2$ represents a suitable leaving group such as a halogen atom (e.g. a fluorine or chlorine atom), with a compound of formula A—M wherein A is as defined above and M is a metal residue such as magnesium halide or lithium in a suitable solvent such as tetrahydrofuran.

Compounds of formula (III) and (IV) are either known in the literature or can be prepared by known methods.

Pharmaceutically acceptable salts may be prepared conventionally by reaction with the appropriate acid or acid derivative.

Compounds of formula (I) and their pharmaceutically acceptable salts have affinity for the 5-$HT_6$ receptor and are believed to be of potential use in the treatment of certain CNS disorders such as anxiety, depression, epilepsy, obsessive compulsive disorders, migraine, cognitive memory disorders (e.g. Alzheimers disease, age related cognitive decline and mild cognitive impairment), Parkinsons Disease, ADHD (Attention Deficit Disorder/Hyperactivity Syndrome), sleep disorders (including disturbances of Circadian rhythm), feeding disorders such as anorexia and bulimia, panic attacks, withdrawal from drug abuse such as cocaine, ethanol, nicotine and benzodiazepines, schizophrenia (in particular cognitive deficits of schizophrenia), stroke and also disorders associated with spinal trauma and/or head injury such as hydrocephalus. Compounds of the invention are also expected to be of use in the treatment of certain GI (gastrointestinal) disorders such as IBS (Irritable Bowel Syndrome). Compounds of the invention are also expected to be of use in the treatment of obesity.

Thus the invention also provides a compound of formula (I) or a pharmaceutically acceptable salt thereof, for use as a therapeutic substance, in particular in the treatment or prophylaxis of the above disorders. In particular the invention provides for a compound of formula (I) or a pharmaceutically acceptable salt thereof, for use in the treatment of depression, anxiety, Alzheimers disease, age related cognitive decline, ADHD, obesity, mild cognitive impairment, schizophrenia, cognitive deficits in schizophrenia and stroke.

The invention further provides a method of treatment or prophylaxis of the above disorders, in mammals including humans, which comprises administering to the sufferer a therapeutically effective amount of a compound of formula (I) or a pharmaceutically acceptable salt thereof.

5-HT$_6$ antagonists have the potential to be capable of increasing basal and learning-induced polysialylated neuron cell frequency in brain regions such as the rat medial temporal lobe and associated hippocampus, as described in WO 03/066056. Thus, according to a further aspect of the present invention, we provide a method of promoting neuronal growth within the central nervous system of a mammal which comprises the step of administering a compound of formula (I) or a pharmaceutically acceptable salt thereof.

In another aspect, the invention provides the use of a compound of formula (I) or a pharmaceutically acceptable salt thereof in the manufacture of a medicament for use in the treatment or prophylaxis of the above disorders.

In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 200 mg, for example 20 to 40 mg; and such unit doses will preferably be administered once a day, although administration more than once a day may be required; and such therapy may extend for a number of weeks or months.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

DESCRIPTION 1

3-Bromophenylsulfonyl fluoride (D1)

To a stirred solution of 3-bromophenylsulfonyl chloride (5 g, 0.0196 mol) in acetonitrile (20 ml) was added potassium fluoride (2.27 g, 0.0391 mol) followed by 18-crown-6 ether (0.08 g) and the reaction stirred at room temperature for 18 h. The reaction mixture was then washed with water (60 ml), extracted with ethyl acetate (3×80 ml) and the combined organic extracts dried (Na$_2$SO$_4$). Solvents were evaporated in vacuo to give a yellow oil (3.79 g, 81%).
$^1$H NMR (CDCl$_3$): δ 7.55 (1H, t), 7.92 (1H, d), 7.95 (1H, d), 8.14 (1H, s).

DESCRIPTION 2

3-Phenylsulfonylbromobenzene (D2)

To a stirred solution of 3-bromophenylsulfonyl fluoride (D1) (1 g, 4.18 mmol) in dry THF (20 ml) at −78° C., under argon was added phenylmagnesium bromide (1M, 1.4 ml, 4.18 mmol) dropwise. The reaction was left to warm to room temperature overnight and then quenched with ammonium chloride (50 ml), extracted with ethyl acetate (3×40 ml) and the combined organic extracts dried (Na$_2$SO$_4$). Solvents were evaporated in vacuo to give a colourless solid (1.09 g, 88%).

$^1$H NMR (CDCl$_3$): δ 7.40 (1H, t), 7.50-7.55 (2H, m), 7.60 (1H, d), 7.69 (1H, d), 7.86 (1H, d), 7.93 (2H, d), 8.08 (1H, s).

DESCRIPTION 3

1-(3-Phenylsulfonylphenyl)-4-tert-butyloxycarbonyl piperazine (D3)

A solution of 2 2,2'-bis(diphenylphosphino)-1,1'-binaphthyl (BINAP) (62 mg, 0.1 mmol) and cesium carbonate (329 mg, 1.01 mmol) in dry dioxane (2 ml) were sonicated for 45 min, under argon. To this solution was added 3-phenylsulfonylbromobenzene (D2) (200 mg, 0.67 mmol) and 1-(tert-butyloxycarbonyl)piperazine (314 mg, 1.68 mmol) and the reaction heated at 100° C. for 18 h. The reaction mixture was evaporated in vacuo and the residue partitioned between water (50 ml) and dichloromethane (50 ml). The organic layer was washed with sat. sodium hydrogen carbonate (50 ml), 10% citric acid (50 ml), brine (50 ml) and then dried (MgSO$_4$). Solvents evaporated in vacuo and the residue purified by column chromatography (silica gel; 0-60% ethyl acetate/petroleum ether) to give the product as a colourless oil (192 mg, 71%)

$^1$H NMR (CDCl$_3$): δ 1.48 (9H, s), 3.15-3.20 (4H, t), 3.55-3.60 (4H, t), 7.05 (1H, m), 7.36 (2H, m), 7.45 (1H, m), 7.50 (2H, m), 7.56 (1H, m), 7.94 (2H, d).

Mass Spectrum: C$_{21}$H$_{26}$N$_2$SO$_4$ requires 402; found: 403 (MH$^+$).

DESCRIPTION 4

4-(3-Phenylsulfonyl-2-chlorophenyl)piperazine-1-carboxylic acid tert-butyl ester (D4A) and 4-(5-Phenylsulfonyl-2-chlorophenyl)piperazine-1-carboxylic acid tert-butyl ester (D4B)

1-(3-Phenylsulfonylphenyl)-4-tert-butyloxycarbonyl piperazine (D3) (84 mg, 0.20 mmol) was dissolved in acetic acid (5 ml) and heated at 60° C. Then N-chlorosuccinimide (28 mg, 0.20 mmol) was added and the stirred reaction mixture was heated at 60° C. for 24 h, then cooled to ambient temperature. The reaction mixture was diluted in dichloromethane and neutralised by addition of an aqueous solution of NaHCO$_3$. The organic layer was dried with MgSO$_4$ and evaporated in vacuo to give two main products, which were separated by column chromatography eluting with dichloromethane/ethyl acetate (0-30%).

Product D4A: 18 mg.

$^1$H-NMR (CDCl$_3$): δ 1.46 (9H, s), 2.92 (4H, t), 3.53 (4H, t), 7.26 (1H, dd), 7.44 (1H, t), 7.50 (2H, tt), 7.59 (1H, tt), 7.94 (2H, dd), 8.10 (1H, dd).

Mass Spectrum: C$_{21}$H$_{25}$$^{35}$ClN$_2$O$_4$S requires 436; Found 437 (MH$^+$).

Product D4B: 40 mg.

$^1$H-NMR (CDCl$_3$): δ 1.49 (9H, s), 3.01 (4H, t), 3.59 (4H, t), 7.47 (1H, d), 7.49-7.54 (3H, m), 7.55 (1H, d), 7.58 (1H, tt), 7.92 (2H, m).

Mass Spectrum: C$_{21}$H$_{25}$$^{35}$ClN$_2$O$_4$S requires 436; Found 437 (MH$^+$).

EXAMPLE 1

1-(3-Phenylsulfonyl-phenyl)piperazine (E1)

A solution of 1-(3-phenylsulfonylphenyl)-4-tert-butyloxycarbonyl piperazine (D3) (96 mg, 0.23 mmol) in 1,4-dioxane (3 ml) and 4M HCl (3 ml) was refluxed at 60° C. for 1 h. The solvents were then evaporated in vacuo and the product dried under high vacuum to give a yellow solid (69 mg, 96%)

$^1$H NMR (DMSO-d$_6$): δ 1.49 (9H, s), 3.21 (4H, m), 3.44-3.47 (4H, m), 7.26 (1H, d), 7.37 (1H, d), 7.45-7.50 (2H, m), 7.60-7.65 (2H, m), 7.65-7.70 (1H, m), 7.95-7.98 (2H, d), 9.15 (2H, br-s).

Mass Spectrum: C$_{16}$H$_{18}$N$_2$SO$_2$ requires 302; found: 303 (MH$^+$).

EXAMPLE 2

1-(3-Phenylsulfonyl-2-chlorophenyl)piperazine (E2)

4-(3-Phenylsulfonyl-2-chlorophenyl)piperazine-1-carboxylic acid tert-butyl ester (D4A) was dissolved in 8 ml of 1,4-dioxane/4 M HCl 1:1. The mixture was heated at 60° C. for 1 h. The solvent was evaporated in vacuo to give the title product as a colourless solid.

$^1$H-NMR (CD$_3$OD): 3.21-3.35 (8H, m), 7.53-7.69 (5H, m), 7.90 (2H, d), 8.14 (1H, d).

Mass Spectrum: C$_{16}$H$_{17}$$^{35}$ClN$_2$O$_2$S requires 336; Found 337 (MH$^+$).

EXAMPLE 3

1-(5-Phenylsulfonyl-2-chlorophenyl)piperazine (E3)

4-(5-Phenylsulfonyl-2-chlorophenyl)piperazine-1-carboxylic acid tert-butyl ester (D4B) was dissolved in 8 ml of 1,4-dioxane/4 M HCl 1:1. The mixture was heated at 60° C. for 1 h. The solvent was evaporated in vacuo to give the title product as a colourless solid.

$^1$H-NMR (CD$_3$OD): 3.29-3.59 (8H, m), 7.57-7.70 (6H, m), 7.97 (2H, d).

Mass Spectrum: C$_{16}$H$_{17}$$^{35}$ClN$_2$O$_2$S requires 336; Found 337 (MH$^+$).

Pharmacological Data

Compounds can be tested following the procedures outlined in WO98/27081. The compounds of Examples E1-E3 were tested and showed good affinity for the 5-HT$_6$ receptor, having pKi values >7.5 at human cloned 5-HT$_6$ receptors, in particular the compounds of Examples E1-E2 had pKi values >8.0.

What is claimed is:

1. A compound of formula (I) or a pharmaceutically acceptable salt thereof:

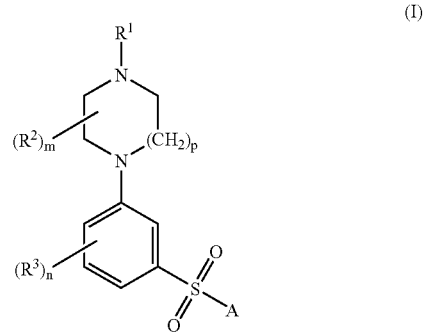

wherein:
R$^1$ and R$^2$ independently represent hydrogen or C$_{1-6}$alkyl;
R$^3$ independently represents hydrogen or halogen;
m and n both represent 1; and
p represents 1 or 2.

2. A compound as defined in claim 1 which is
1-(3-Phenylsulfonyl-phenyl)piperazine;
1-(3-Phenylsulfonyl-2-chlorophenyl)piperazine; or
1-(5-Phenylsulfonyl-2-chlorophenyl)piperazine;
or a pharmaceutically acceptable salt thereof.

3. A pharmaceutical composition which comprises a compound as defined in claim 1 and a pharmaceutically acceptable carrier or excipient.

4. A method of treating depression, obesity, mild cognitive impairment, and schizophrenia which comprises administering a therapeutically effective amount to a patient in need thereof of a compound of formula (I) as defined in claim 1 or a pharmaceutically acceptable salt thereof.

* * * * *

UNITED STATES PATENT AND TRADEMARK OFFICE
CERTIFICATE OF CORRECTION

PATENT NO. : 7,262,188 B2  Page 1 of 1
APPLICATION NO. : 10/547987
DATED : August 28, 2007
INVENTOR(S) : Gregor James MacDonald and Mervyn Thompson It is certified that error appears in the above-identified patent and that said Letters Patent is hereby corrected as shown below:

In column 8, lines 55 through 65, the structure depicting formula (I) should be replaced with the following:

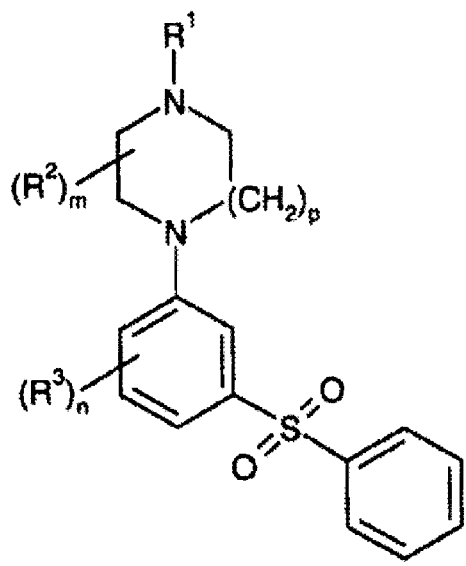

Signed and Sealed this

Fifth Day of August, 2008

JON W. DUDAS
*Director of the United States Patent and Trademark Office*